United States Patent
Mensch et al.

(10) Patent No.: US 11,717,170 B2
(45) Date of Patent: Aug. 8, 2023

(54) BODY CORE TEMPERATURE SENSOR WITH TWO TEGS

(71) Applicant: Robert Bosch GmbH, Stuttgart (DE)

(72) Inventors: Beatrix Mensch, Illertissen (DE); Thomas Rocznik, Mountain View, CA (US); Christian Peters, Sunnyvale, CA (US); Seow Yuen Yee, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 278 days.

(21) Appl. No.: 16/957,257

(22) PCT Filed: Dec. 26, 2018

(86) PCT No.: PCT/US2018/067495
§ 371 (c)(1),
(2) Date: Jun. 23, 2020

(87) PCT Pub. No.: WO2019/133601
PCT Pub. Date: Jul. 4, 2019

(65) Prior Publication Data
US 2020/0390336 A1 Dec. 17, 2020

Related U.S. Application Data

(60) Provisional application No. 62/611,002, filed on Dec. 28, 2017.

(51) Int. Cl.
*A61B 5/01* (2006.01)
*A61B 5/00* (2006.01)

(52) U.S. Cl.
CPC .............. *A61B 5/01* (2013.01); *A61B 5/0008* (2013.01); *A61B 5/6801* (2013.01); *A61B 5/742* (2013.01);
(Continued)

(58) Field of Classification Search
None
See application file for complete search history.

(56) References Cited

U.S. PATENT DOCUMENTS

| | | | |
|---|---|---|---|
| 9,532,900 B2 | 1/2017 | Smith et al. | |
| 2006/0056487 A1* | 3/2006 | Kuroda | G01K 1/165 374/E7.042 |
| 2007/0239038 A1* | 10/2007 | Nicolaescu | A61B 5/01 600/549 |
| 2012/0238901 A1 | 9/2012 | Augustine | |

(Continued)

FOREIGN PATENT DOCUMENTS

| | | |
|---|---|---|
| CN | 104983560 A | 10/2015 |
| WO | 2015/200380 A1 | 12/2015 |

OTHER PUBLICATIONS

International Search Report corresponding to PCT Application No. PCT/US2018/067495, dated Apr. 26, 2019 (4 pages).
(Continued)

*Primary Examiner* — Benjamin S Melhus
(74) *Attorney, Agent, or Firm* — Maginot, Moore & Beck LLP

(57) ABSTRACT

In one embodiment a temperature sensor system includes two sensor assemblies with different thermal resistances, each sensor assembly including a temperature sensing portion and a thermoelectric generator portion configured to receive heat flow from a body through the associated temperature sensing portion. A control unit is operably connected to the sensor assemblies and the memory. The control unit is configured to execute program instructions stored in the memory to obtain signals from the temperature sensor portions and the thermoelectric generator portions and to calculate and output a body core temperature (TB) based upon the obtained signals.

3 Claims, 2 Drawing Sheets

(52) U.S. Cl.
CPC .............. *A61B 2560/0214* (2013.01); *A61B 2562/0271* (2013.01); *A61B 2562/16* (2013.01)

(56) References Cited

U.S. PATENT DOCUMENTS

| | | |
|---|---|---|
| 2013/0317388 A1 | 11/2013 | Bieberich et al. |
| 2017/0049397 A1* | 2/2017 | Sun .................. G01K 7/427 |
| 2018/0008149 A1* | 1/2018 | Pekander ............ G01K 7/427 |
| 2018/0049646 A1* | 2/2018 | Ellis .................. A61B 5/01 |
| 2018/0064348 A1* | 3/2018 | Tsuchimoto ......... G01K 13/20 |
| 2018/0356298 A1* | 12/2018 | Atallah ............... G01K 13/20 |
| 2018/0364109 A1* | 12/2018 | Bongers .............. G01K 7/427 |
| 2019/0142280 A1* | 5/2019 | Bongers ............ A61B 5/0002 600/549 |

OTHER PUBLICATIONS

Kitamura, K., et al., "Development of a New Method for the Noninvasive Measurement of Deep Body Temperature Without a Heater," Medical Engineering & Physics, vol. 32, 2010, pp. 1-6, Elsevier Ltd. 2009.

Huang, M. et al., "Theoretical Simulation of the Dual-Heat-Flux Method in Deep Body Temperature Measurements," 32nd Annual International Conference of the IEEE EMBS, pp. 561-564. IEEE 2010.

Huang, M. et al., "Improvement of the Dual-heat-flux Method for Deep Body Temperature Measurement Based on a Finite Element Model," 35th Annual International Conference of the IEEE EMBS, pp. 1202-1205. IEEE 2013.

Huang, M. et al., "Structural Optimization of a Wearable Deep Body Thermometer: From Theoretical Simulation to Experimental Verification," Journal of Sensors, vol. 2016, Article ID 4828093, 7 pages. Hindawi Publishing Corp. 2016.

Feng, J. et al., "Development of an Improved Wearable Device for Core Body Temperature Monitoring Based on the Dual Heat Flux Principle," Physiological Measurement, vol. 38 (2017), pp. 652-668. Institute of Physics and Engineering in Medicine, Mar. 17, 2017.

* cited by examiner

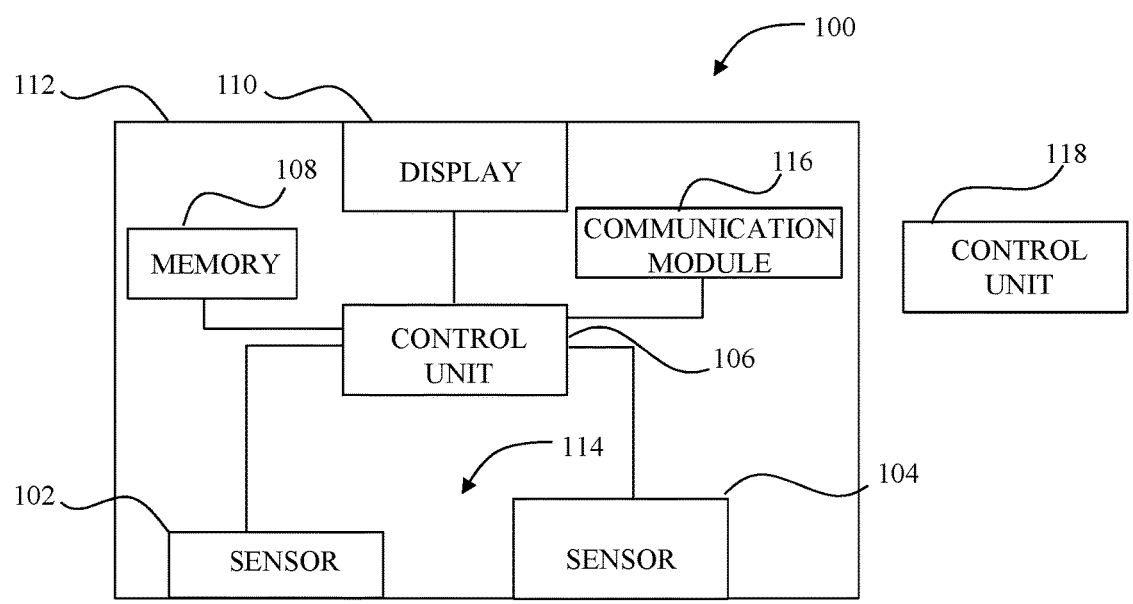
FIG. 1
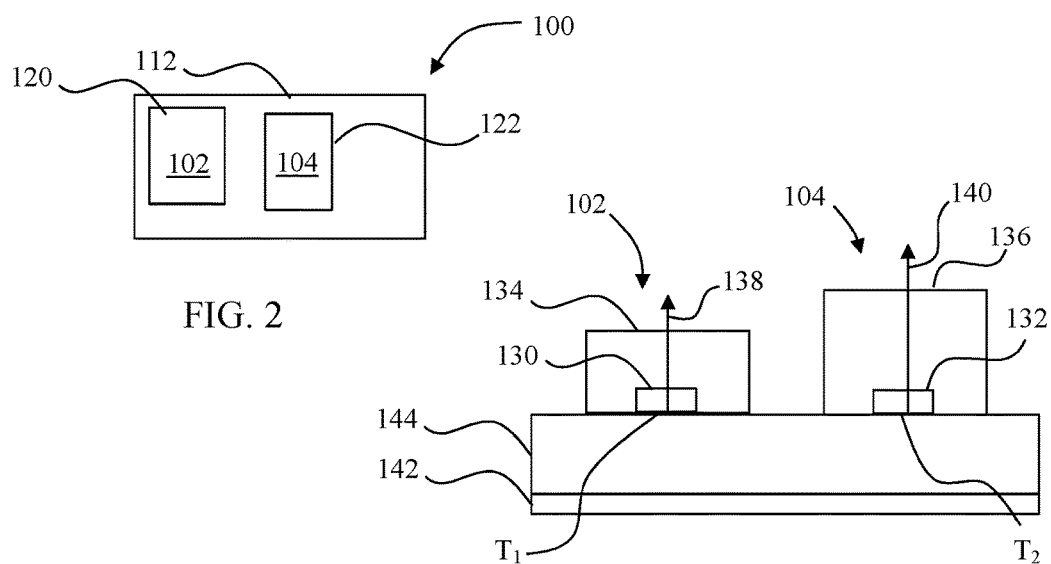
FIG. 2
FIG. 3

BODY CORE TEMPERATURE SENSOR WITH TWO TEGS

This application is a 35 U.S.C. § 371 National Stage Application of PCT/US2018/067495, filed on Dec. 26, 2018, which claims priority to U.S. provisional patent application No. 62/611,002, filed on Dec. 28, 2017 and entitled "MEASURING THE BODY CORE TEMPERATURE WITH TWO TEGS," the disclosures of which are incorporated herein by reference in their entirety.

FIELD

The device and method disclosed in this document relates to thermal sensing and, more particularly, to thermal sensing of core temperatures.

BACKGROUND

It is known to determine the body core temperature of a human with a sensor placed on the skin using a dual heat flux method. According to this known method, a Doppler Sensor is used. The Doppler sensor has two temperature sensors, each on a respective side of the sensor and thermally separated by an insulating layer. The sensor is placed on the skin, so that the temperature between the skin and the bottom surface of the insulating layer is measured and also the temperature on the top surface of the insulating layer. It is assumed that there is a constant and vertical heat flow from the body core to the top surface of the sensor. Thus the heat flow through the sensor is the same as the heat flow through the skin layer below the sensor. The heat flow through the Doppler Sensor can be calculated with Fourier's law:

$$I = \frac{T_S - T_U}{R_I}$$

Where:
"I" is heat flow=heat transfer rate;
"$T_S$" is temperature between skin and the insulating layer;
"$T_U$" is temperature at the top surface of the insulating layer; and
"$R_I$" is thermal resistance of the insulating layer.

The heat flow through the skin layer below the sensor can be calculated as follows:

$$I = \frac{T_B - T_S}{R_S}$$

Where:
"$T_B$" is body core temperature below the skin layer; and
"$R_S$" is thermal resistance of the skin layer.

Since the heat flow through the sensor is the same as the heat flow through the skin layer below the sensor, the above equations can be combined and the body core temperature can be calculated by:

$$T_B = T_S + \frac{(T_S - T_U)R_S}{R_I}$$

The only unknown is thus the thermal resistance of the skin layer. The thermal resistance of a human skin layer, however, is very difficult to determine with a desired accuracy. The problem is exacerbated by the fact that there is a significant difference in thermal resistance for each human and for each location on the body. Thus no generic constant can be applied without introducing some error and the skin resistance must be accounted for.

To eliminate the thermal resistance of the skin in the Doppler Sensor method, two sensors with different thermal resistance values are closely placed on the skin. Because of the different thermal resistance values, different temperatures between the sensors and the skin layer and also on top of the sensors occur. Assuming that the thermal resistance of the skin layer below each of the sensors is the same (since the sensors are closely spaced), the body core temperature can then be calculated with the following equations:

$$T_B = T_1 + \frac{(T_1 - T_3)R_S}{R_1}$$

$$T_B = T_2 + \frac{(T_2 - T_4)R_S}{R_2}$$

The above equations can be combined to:

$$T_B = T_1 + \frac{(T_1 - T_2)(T_1 - T_3)}{K(T_2 - T_4) - (T_1 - T_2)}$$

With $$K = \frac{R_1}{R_2}$$

Therefore the body core temperature can be determined without knowing the thermal properties (thermal resistance) of the skin layer. But with this method the thermal resistance values of both sensors must be known or the factor "K" must be determined with a calibration.

What is needed is a system and method for determining the core temperature of a creature or object which does not require knowledge of the thermal resistance values of the sensors. It would also be beneficial if a system and method for determining the core temperature of a creature or object did not require calibration of the system.

SUMMARY

The present disclosure is directed to a system and method of determining the core temperature of creatures or objects, e.g. humans, animals, machines, etc., using two or more sensors placed on the surface of the object. The system does not require prior knowledge of the thermal properties (thermal resistance) of the object. Each sensor assembly according to the present disclosure has a different thermal resistance and measures the heat flux through the sensor assembly and the temperature between the sensor assembly and the surface on which it is applied. This is implemented for each sensor assembly in one embodiment with a thermoelectric generator (TEG) and a temperature sensor on one side of the TEG. Because the heat flux is measured directly, the thermal resistance values of the sensors are not needed in order to calculate a core temperature. Additionally, there is no need to perform a calibration step.

In one embodiment, a temperature sensor system includes two sensor assemblies with different thermal resistances, each sensor assembly including a temperature sensing portion and a thermoelectric generator portion configured to receive heat flow from a body through the associated temperature sensing portion. A control unit is operably connected to the sensor assemblies and the memory. The control unit is configured to execute program instructions stored in the memory to obtain signals from the temperature sensor portions and the thermoelectric generator portions and to calculate and output a body core temperature ($T_B$) based upon the obtained signals.

In one or more embodiments, the control unit is configured to calculate the body core temperature ($T_B$) based upon the following equation:

$$T_B = \frac{\dot{Q}''_1 \cdot T_{skin,2} - \dot{Q}''_2 \cdot T_{skin,1}}{\dot{Q}''_1 - \dot{Q}''_2}$$

wherein "$\dot{Q}''_1$" is the first heat flow;
"$T_{skin,\,2}$" is the second temperature;
"$\dot{Q}''_2$" is the second heat flow; and
"$T_{skin,\,1}$" is the first temperature.

In one or more embodiments, the first sensor assembly and the second sensor assembly are positioned within a single housing.

In one or more embodiments, the first sensor assembly and the second sensor assembly are spaced apart by a thermal gap.

In one or more embodiments the housing is configured to expose the first sensor assembly and the second sensor assembly to the body through a first side of the housing, and the housing includes at least one window on a side of the housing opposite the first side, the at least one window configured to transfer at least one of the first heat flow and the second heat flow out of the temperature sensor system. A single window is used in some embodiments for both sensor assemblies. In other embodiments, each sensor assembly includes a dedicated window.

In one or more embodiments, the system includes a display, and the control unit is operably connected to the display and configured to execute the program instructions to display the calculated body core temperature with the display.

In one or more embodiments, the first temperature sensing portion substantially surrounds the first thermoelectric generator portion except at the first surface portion, and the second temperature sensing portion substantially surrounds the second thermoelectric generator portion except at the second surface portion.

In one or more embodiments, the difference in thermal resistance is accomplished by providing the thermoelectric generator portions in differing heights.

In one or more embodiments, the difference in thermal resistance is effected by the incorporation of a layer of material in one of the sensor assemblies or in the thermal path through one of the sensor assemblies which adds to the thermal resistance of that sensor assembly.

In accordance with one embodiment, a method of providing a body core temperature includes obtaining signals from the temperature sensor portions and the thermoelectric generator portions of two different sensor assemblies which have different thermal resistances under the control of a control unit. The control unit further executes program instructions in a memory to calculate and output a body core temperature using the obtained signals.

In accordance with one or more methods, the body core temperature ($T_B$) is calculated by the control unit based upon the following equation:

$$T_B = \frac{\dot{Q}''_1 \cdot T_{skin,2} - \dot{Q}''_2 \cdot T_{skin,1}}{\dot{Q}''_1 - \dot{Q}''_2}$$

wherein "$\dot{Q}''_1$" is the first heat flow;
"$T_{skin,\,2}$" is the second temperature;
"$\dot{Q}''_2$" is the second heat flow; and
"$T_{skin,\,1}$" is the first temperature.

In accordance with one or more embodiments, a method of providing a body core temperature further includes providing the first sensor assembly and the second sensor assembly in a single temperature sensor system housing, and supporting the temperature sensor system housing on the body.

In accordance with one or more embodiments, providing the first sensor assembly and the second sensor assembly in the single housing includes providing the first sensor assembly and the second sensor assembly in the single temperature sensor system housing with the first sensor assembly and the second sensor assembly spaced apart within the single housing by a thermal gap.

In accordance with one or more embodiments, providing the first sensor assembly and the second sensor assembly in the single housing includes providing the first sensor assembly and the second sensor assembly in the single temperature sensor system housing with the first thermoelectric generator portion substantially surrounding first temperature sensing portion except at the first surface portion. These embodiments further include providing the first sensor assembly and the second sensor assembly in the single temperature sensor system housing with the second thermoelectric generator portion substantially surrounding second temperature sensing portion except at the second surface portion.

In accordance with one or more embodiments, supporting the housing on the body includes exposing the first sensor assembly and the second sensor assembly to the body through a first side of the housing. In one or more of these embodiments, the method further includes transferring at least one of the first heat flow and the second heat flow out of the temperature sensor system housing through at least one window on a side of the housing opposite the first side.

In accordance with one or more embodiments, a method of providing a body core temperature further includes displaying, under the control of the control unit, the calculated body core temperature on a display.

BRIEF DESCRIPTION OF THE DRAWINGS

The foregoing aspects and other features are explained in the following description, taken in connection with the accompanying drawings.

FIG. 1 shows schematic side cross-sectional view of a system which can be used to determine the body core temperature of creatures or objects.

FIG. 2 depicts a top plan view of the system of FIG. 1.

FIG. 3 depicts a simplified side plan view of the sensor assemblies of the system of FIG. 1.

DETAILED DESCRIPTION

Figure 4:
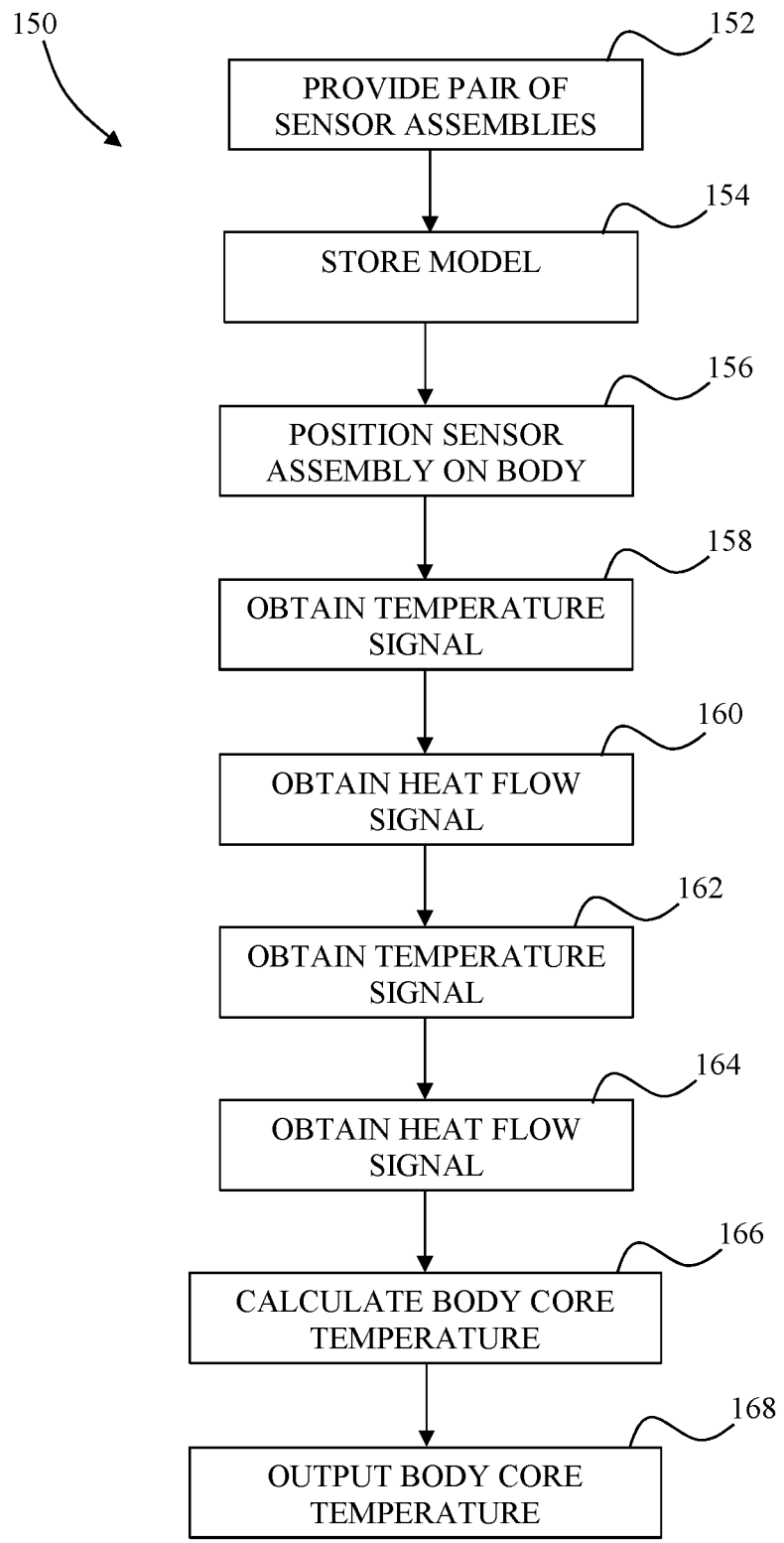
FIG. 4 depicts a procedure which can be used to calculate a body core temperature using the system of FIG. 1.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

FIG. 1 depicts a system 100 which includes two sensor assemblies 102 and 104, a control unit 106, memory 108, and an output device 110 which in one embodiment is a display. In some embodiments, one or more of the control unit 106 and the display 110 is located remotely from sensor assemblies 102/104. In one embodiment, both sensor assemblies 102/104 are supported by a single housing 112 with a thermal gap 114 between the sensor assemblies. The thermal gap in one embodiment is an air or vacuum gap. In another embodiment, the thermal gap includes an insulator material selected to thermally isolate the two sensor assemblies 102/104 from each other. FIG. 1 further depicts a communications module 116 and a remote control unit 118 which are included in some embodiments.

While schematically depicted as within the housing 112 in FIG. 1, the sensor assemblies 102/104 are positioned such that there is no impediment to heat flow through the upper surface of the sensor assemblies 102/104. Thus, FIG. 2 depicts the system 100 with a window 120 which thermally exposes the upper surface of the sensor assembly 102 and a window 122 which thermally exposes the upper surface of the sensor assembly 104. The windows 120/122 in some embodiments are openings in the housing 112 which directly expose the upper surface of the sensor assemblies 102/104 to ambient air. In other embodiments, one or more of the windows 120/122 comprises a material with a high thermal conductivity. In some embodiments, the lower surfaces of the sensor assemblies 102/104 likewise include windows 120/122.

The control unit 106 is operably connected to the sensor assemblies 102/104, the memory 108, communications module 116, and the display 110. The control unit 106 is a control device which in different embodiments includes one or more integrated circuits (ICs), such as microcontrollers (small, complete computer systems, for example with its own processor and memory, which are formed as a single integrated circuit), application specific integrated circuits (ASIC), application-specific standard products (ASSP), and the like. The control unit 106 is configured to execute program instructions stored within the memory 108, which in some embodiments is a part of the control unit 106, to obtain signals from the sensor assemblies 102/104, to determine the body core temperature of creatures or objects using the obtained signals, and to control the display unit to display the determined core temperatures. In some embodiments, the remote control unit 118 is configured like the control unit 106 and performs at least some of the functions described with respect to the control unit 106.

In some embodiments, the system 100 includes a communication module 116, in addition to or as an alternative to the display unit, which provides for external communication, either wired or wireless, of the obtained signals and/or the determined body core temperatures. The communicated signals are then used by the external control unit 118 to determine the body core temperature of a creature or object.

The sensor assemblies 102/104 are shown in further detail in FIG. 3. The sensor assemblies 102/104 include respective temperature sensing portions 130/132 and thermoelectric generator (TEG) portions 134/136. The temperature sensing portions 130/132 are each positioned in one embodiment so as to be positioned directly on the outer surface of the skin of a creature or object and configured to provide a respective signal to the control unit 106 representative of the temperature of the creature or object.

The temperature sensing portions 130/132 and the TEG portions 134/136 are further configured to minimize interference with transfer of heat through the sensor assemblies 102/104. To this end, the TEG portions 134/136 in this embodiment substantially surround the temperature sensing portions 130/132 with the exception of the surface portions of the temperature sensing portions 130/132 which are configured to receive heat flow from a body. Some relatively small surfaces (not shown) which provide for electrical connection to the temperature sensing portions 130/132 may also not be covered by the TEG portions 134/136.

Accordingly, heat is transferred from an underlying substrate substantially directly through the temperature sensing portions 130/132 and the TEG portions 134/136 and out of the upper surface of the TEG portions 134/136 as indicated by arrows 138 and 140. Depending upon the thermal conditions, heat flux can also be in the opposite direction.

The TEG portions 134/136 are solid state portions that convert heat flux (temperature differences) directly into a voltage signal through a phenomenon called the Seebeck effect (a form of thermoelectric effect). In one embodiment, the TEG is used as a sensor rather than an energy sensor with the output signal provided to the control unit. In some embodiments, the TEG is further used as an energy source.

The control unit 106 in one embodiment executes the stored program instructions to determine heat flux using the electrical energy from the TEG portions 134/136 and the signals from the temperature sensing portions 130/132. The stored program instructions in one embodiment reflect the assumptions that the thermal resistance of the skin layer below each of the sensor assemblies is the same, and that there is a constant and vertical heat flow from the body core to the top surface of the sensor or in the opposite direction. Consequently the heat flux through the sensor assemblies is the same as the heat flux through the skin layer below the sensors. Accordingly, heat flux through the skin layer can be calculated with Fourier's law:

$$\dot{Q}'' = \frac{T_B - T_{skin}}{R_{th,skin} \cdot A}$$

Where:
"$\dot{Q}''$" is heat flux through the skin layer (and through the sensor);
"$T_{skin}$" is the temperature between the skin and the sensor;
"$R_{th,skin}$" is the thermal resistance of the skin; and
"A" is the area of the sensor.

Thus, if skin resistance were known, the body core temperature would be calculated as follows:

$$T_B = \dot{Q}'' \cdot R_{th,Skin} \cdot A + T_{skin}$$

According to Fourier's law the body core temperature can be calculated with either the measurements of the first or the second sensor when the thermal resistance of the skin is known according to the following equations:

$$T_B = \dot{Q}''_1 \cdot R_{th,skin} \cdot A + T_{skin,1}$$

$$T_B = \dot{Q}''_2 \cdot R_{th,skin} \cdot A + T_{skin,2}$$

In order to avoid use of skin resistance in the calculation, the TEG portions 134/136 are equal in the embodiment depicted except for the height as depicted in FIG. 3 (the remainder of the system 100 is omitted for clarity). Because of the different height the TEG portions 134/136 have a different thermal resistance resulting in a difference in thermal resistance between the sensor assemblies. Thus, even with a single body core temperature at the body core 142, two different heat profiles are exhibited within the sensor assemblies 102/104 and two different skin temperatures ($T_{skin,\,1}$ and $T_{skin,\,2}$) result at the surface of the skin 144 below the temperature sensors 130/132. That is, the shorter sensor assembly 102 will pass heat more easily resulting in a lower temperature $T_{skin}$ below the temperature sensor 130 and a reduced heat profile within the TEG portion 134.

Since the sensor assembly configuration provides two different heat profiles and two different sensed temperatures, the above equations can be combined so that the thermal resistance of the skin can be canceled out resulting in the following equation:

$$T_B = \frac{\dot{Q}_1'' \cdot T_{skin,2} - \dot{Q}_2'' \cdot T_{skin,1}}{\dot{Q}_1'' - \dot{Q}_2''}$$

While in the embodiment of FIG. 3 a difference in height is used as a variable to achieve a difference in thermal resistance, other differences are used in various embodiments to realize a difference in thermal resistance. Some variables that are used in different embodiments to achieve different thermal resistances, alone or in combination with other variables, include use of different materials with different thermal resistances, using different thermal paths, adding a resistive layer with a known thermal resistance to one of the assemblies, etc. Accordingly, the "thermal resistance" of a sensor assembly is the thermal resistance in the heat flow path from the outer skin of the body, through the temperature sensor portion and the TEG portion, and out of the sensor system.

Accordingly, the control unit 106 determines the body core temperature of a creature based upon the above equation by executing the stored program instructions.

The body core temperature of an object is likewise calculated using the foregoing equation since the "skin" is defined to include "surface" in each of the above equations. Thus, the system 100 can not only be applied to humans but also to any body including creatures or objects e.g. animals or machines, to determine a core temperature. Accordingly, as used herein, the "skin" or "outer skin" (these terms are used interchangeably except where noted) of a body therefore means all substances through which heat flows from the core of the body to the sensor assembly. Thus, when the sensor is placed upon a piece of clothing worn by an individual, the clothing is considered to be part of the individual's "outer skin". Likewise, when the sensor is placed upon a tank or pipe, the tank or pipe material is considered to be part of the "outer skin".

FIG. 4 depicts a method 150 of operation of the system 100. At block 152, a pair of sensor assemblies with different thermal resistances is provided. In some embodiments, this is accomplished by using identical TEGs and incorporating a material with a known thermal resistance to one of the TEGs to modify the thermal resistance of one of the TEGs. The material in some embodiments is the same material used in forming the TEG such that one TEG has a greater height than the other TEG. In some embodiments, different models of TEGs are used, the different models having different thermal resistances. In some embodiments, the TEGS are specifically manufactured differently to provide the different thermal resistances such as by modifying the physical shape (e.g., greater height), incorporating different materials in the TEG, etc. In one preferred embodiment, the pair of sensor assemblies is housed in a single housing.

At block 154 the thermal model for the sensor system is stored in an appropriate memory such as the memory 108. The model is based upon the following equation:

$$T_B = \frac{\dot{Q}_1'' \cdot T_{skin,2} - \dot{Q}_2'' \cdot T_{skin,1}}{\dot{Q}_1'' - \dot{Q}_2''}$$

which was described above. The sensor assemblies are then positioned on the body for which a temperature is to be determined at block 156.

Upon activation, the control unit for the system obtains a temperature signal (block 158) and a heat flow signal (block 160) from one of the two sensor assemblies. The control unit further obtains a temperature signal (block 162) and a heat flow signal (block 164) from the other sensor assembly. The control unit then executes program instructions stored in the memory to calculate a body core temperature (block 166) using the model stored at block 154. The control unit then outputs the calculated body core temperature (block 168) such as by causing the temperature to be displayed either on a display or other output device local to the sensor assembly, or at a remote output device. In some embodiments, the output is directed to a memory where it is stored pending a future transfer of the data.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

The invention claimed is:

1. A temperature sensor system, comprising:
   a first sensor assembly including
   (i) a first temperature sensing portion configured to generate a first temperature signal based upon a first temperature of a body proximate a first surface portion of the first temperature sensing portion,
   and (ii) a first thermoelectric generator portion configured to receive a first heat flow from the body through the first temperature sensing portion and to generate a first heat flow signal based upon the first heat flow,
   the first sensor assembly having a first thermal resistance;
   a second sensor assembly including
   (i) a second temperature sensing portion configured to generate a second temperature signal based upon a second temperature of the body proximate a second surface portion of the second temperature sensing portion,
   and (ii) a second thermoelectric generator portion configured to receive a second heat flow from the body through the second temperature sensing portion and to generate a second heat flow signal based upon the second heat flow,
   the second sensor assembly having a second thermal resistance different from the first thermal resistance;
   a memory including program instructions stored therein;
   and a control unit operably connected to the first sensor assembly, the second sensor assembly, and the memory, the control unit configured to execute the program instructions to
obtain the first temperature signal, the first heat flow signal, the second temperature signal and the second heat flow signal,
calculate a body core temperature ($T_B$) based upon the obtained first temperature signal, the obtained first heat flow signal, the obtained second temperature signal, and the obtained second heat flow signal,
and output the calculated body core temperature, wherein the control unit is configured to calculate the body core temperature (TB) based upon the following equation:

$$T_B = \frac{\dot{Q}''_1 \cdot T_{skin,2} - \dot{Q}''_2 \cdot T_{skin,1}}{\dot{Q}''_1 - \dot{Q}''_2}$$

wherein "$\dot{Q}_1''$" is the first heat flow;
"$T_{skin,\,2}$" is the second temperature;
"$\dot{Q}_2''$" is the second heat flow; and
"$T_{skin,\,1}$" is the first temperature;
the first sensor assembly and the second sensor assembly are positioned within a single housing
the first sensor assembly and the second sensor assembly are spaced apart by a thermal gap;
the housing is configured to expose the first sensor assembly and the second sensor assembly to the body through a first side of the housing;
the housing includes at least one window on a side of the housing opposite the first side,
the at least one window configured to transfer at least one of the first heat flow and the second heat flow out of the temperature sensor system;
the first thermoelectric generator portion substantially surrounds the first temperature sensing portion except at the first surface portion;
the second thermoelectric generator portion substantially surrounds the second temperature sensing portion except at the second surface portion;
the first thermoelectric generator portion extends for a first distance between the first side and the side of the housing opposite the first side;
the second thermoelectric generator portion extends for a second distance between the first side and the side of the housing opposite the first side;
and the second distance is greater than the first distance.

2. The temperature sensor system of claim 1, further comprising:
a display, wherein the control unit is operably connected to the display and wherein the control unit is configured to execute the program instructions to display the calculated body core temperature with the display.

3. A temperature sensor system, comprising:
a first sensor assembly including
(i) a first temperature sensing portion configured to generate a first temperature signal based upon a first temperature of a body proximate a first surface portion of the first temperature sensing portion,
and (ii) a first thermoelectric generator portion configured to receive a first heat flow from the body through the first temperature sensing portion and to generate a first heat flow signal based upon the first heat flow,
the first sensor assembly having a first thermal resistance;
a second sensor assembly including
(i) a second temperature sensing portion configured to generate a second temperature signal based upon a second temperature of the body proximate a second surface portion of the second temperature sensing portion,
and (ii) a second thermoelectric generator portion configured to receive a second heat flow from the body through the second temperature sensing portion and to generate a second heat flow signal based upon the second heat flow,
the second sensor assembly having a second thermal resistance different from the first thermal resistance;
a memory including program instructions stored therein,
and a control unit operably connected to the first sensor assembly, the second sensor assembly, and the memory,
the control unit configured to execute the program instructions to
obtain the first temperature signal, the first heat flow signal, the second temperature signal and the second heat flow signal,
calculate a body core temperature ($T_B$) based upon the obtained first temperature signal, the obtained first heat flow signal, the obtained second temperature signal, and the obtained second heat flow signal,
and output the calculated body core temperature,
wherein the control unit is configured to calculate the body core temperature (TB) based upon the following equation:

$$T_B = \frac{\dot{Q}''_1 \cdot T_{skin,2} - \dot{Q}''_2 \cdot T_{skin,1}}{\dot{Q}''_1 - \dot{Q}''_2}$$

wherein "$\dot{Q}_1''$" is the first heat flow;
"$T_{skin,\,2}$" is the second temperature;
"$\dot{Q}_2''$" is the second heat flow; and
"$T_{skin,\,1}$" is the first temperature;
the first sensor assembly and the second sensor assembly are positioned within a single housing
the first sensor assembly and the second sensor assembly are spaced apart by a thermal gap;
the housing is configured to expose the first sensor assembly and the second sensor assembly to the body through a first side of the housing;
the housing includes at least one window on a side of the housing opposite the first side,
the at least one window configured to transfer at least one of the first heat flow and the second heat flow out of the temperature sensor system;
the first thermoelectric generator portion substantially surrounds the first temperature sensing portion except at the first surface portion,
the second thermoelectric generator portion substantially surrounds the second temperature sensing portion except at the second surface portion;
the second sensor assembly includes a layer of material having a third thermal resistance;
and the first sensor assembly does not include a layer of the material, such that the second thermal resistance is greater than the first thermal resistance by an amount of the third thermal resistance.

* * * * *